United States Patent [19]
Mascarenhas

[11] Patent Number: 5,459,051
[45] Date of Patent: Oct. 17, 1995

[54] METHODS AND VECTORS FOR OVER-EXPRESSION OF UBIQUITIN FUSION PROTEINS IN HOST CELLS

[75] Inventor: Desmond Mascarenhas, San Rafael, Calif.

[73] Assignee: Celtrix Pharmaceuticals, Inc., Santa Clara, Calif.

[21] Appl. No.: 101,506

[22] Filed: Aug. 2, 1993

Related U.S. Application Data

[63] Continuation-in-part of Ser. No. 37,597, Mar. 26, 1993, abandoned.

[51] Int. Cl.$^6$ .......................... C12N 15/67; C12N 15/70; C12N 15/87
[52] U.S. Cl. .................. 435/69.7; 435/320.1; 435/69.1; 435/69.5; 435/69.6; 435/69.4; 435/68.1
[58] Field of Search ............................... 435/320.1, 69.1, 435/69.5, 69.6, 69.7, 69.4

[56] References Cited

U.S. PATENT DOCUMENTS

| | | | |
|---|---|---|---|
| 4,886,747 | 12/1989 | Derynck et al. | 435/69.4 |
| 5,084,384 | 1/1992 | Wong et al. | 435/69.4 |
| 5,187,151 | 2/1993 | Clark et al. | 514/3 |

FOREIGN PATENT DOCUMENTS

| | | | |
|---|---|---|---|
| 0369861A2 | 5/1990 | European Pat. Off. | |
| 0413440 | 2/1991 | European Pat. Off. | C12N 15/61 |
| WO88/02406 | 4/1988 | WIPO . | |
| WO89/12678 | 12/1989 | WIPO . | |

OTHER PUBLICATIONS

Buchner, J., et al. (1991) "Routes to active proteins from transformed microorganisms", *Curr. Opinion Biotechnol.* 2(4): 532–538.
Schein, C. H. (1989) "Production of soluble recombinant proteins in bacteria" *Biotechnology*, 7:1141–1149.
Butt, T. R., et al. (1989) "Ubiquitin fusion augments the yield of cloned gene products in *Escherichi coli*", *Proc. Natl. Acad. Sci. USA* 86:2540–2544.
Power, R. F., et al. (1990) "High–Level Expression of a Truncated Chicken Progesterone Receptor in *Escherichia coli*", *J. Biol. Chem.* 265:1419–1424.
Hlodan, R., et al. (1991) "Protein Folding and its Implications for the Production of Recombinant Proteins", *Biotechnol. Genet. Engr. Rev.* 9:47–88.
Smith, D. H., et al., "Blocking of HIV–1 infectivity by a soluble, secreted for of the CD4 antigen" *Science* (1987) 238:1704–1707.
López–Casillas, F., et al., "Structure and expression of the membrane proteoglycan betaglycan, a component of the TGF–β receptor system" *Cell* (1991) 67:785–795.
Lui, M. A. et al., "Transforming growth factor–β–Mullerian inhibiting substance family of growth regulators" *Cancer Investigation* (1991) 9(3):325–336.
Whalen, G. F., "Solid tumours and wounds: transformed cells misunderstood as injured tissue?" *Lancet* (1990) 336:1489–1492.

Wilder, R. L., et al., "Transforming growth factor–β in rheumatoid arthritis" *Annals New York Academy of Sciences* (1990) 593:197–207.
Roberts, A. B., et al., "Chapter 8: The Transforming Growth Factor–βs", in *Handbook Exp. Pharm., Peptide Growth Factors and Their Receptors I*, Sporn, M. B., et al., editors, (published by Springer–Verlag, New York, 1990), vol. 95, pp. 419–458.
Wahl, S. M., et al., "Inflammatory and Immunomodulatory Roles of TGF–β", *Immunology Today* (1989) 10(8):258–261.
Kim, S–J., et al, "Autoinduction of Transforming Growth Factor β1 Is Mediated By the AP–1 Complex", *Mol. Cell. Biol.* (1990) 10(4):1492–1497.
Mauer, S. M., et al., "Structural–Functional Relationships in Diabetic Nephropathy", *J. Clin. Invest.* (1984) 74:1143–1155.
Canney, P. A., et al., "Transforming Growth Factor Beta: A Promoter of Late Connective Tissue Injury Following Radiotherapy", *British J. Radiol.* (1990) 63:620–623.
Border, W. A., et al., "Suppression of Experimental Glomerulonephritis by Antiserum Against Transforming Growth Factorβ1", *Nature* (199) 346:371–374.
Border, W. A., et al., "Antagonists of Transforming Growth Factor–β: A Novel Approach to Treatment of Glomerulonephritis and Prevention of Glomerulosclerosis", *Kidney Int.* (1992) 41:566–570.
Wahl, S. M., et al., "Reversal of Acute and Chronic Synovial Inflammation by Anti–Transforming Growth Factor Beta", *J. Exp. Med.* (1993) 177(1):225–230.
Wahl, S. M., "Transforming Growth Factor Beta (TGF–β) in Inflammation: A Cause and a Cure", *J. Clin. Immunol.* (1992) 12(2):1–14.
Goddard, D. H., et al., "Autocrine Regulation of Rheumatoid Arthritis Synovial Cell Growth in Vitro", *Cytokine* (1990) 2:149–155.
Shah, M., et al., "Control of Scarring in Adult Wounds by Neutralizing Antibody to Transforming Growth Factor β", *The Lancet* (1992) 339:213–214.
Kekow, J., et al., "Transforming Growth Factor β and Noncytopathic Mechanisms of Immunodeficiency in Human Immunodeficiency Virus Infection", *Proc. Natl. Acad. Sci. USA* (1990) 87:8321–8325.
Steiner, M. S., "Transforming Growth Factor–β1 Overproduction in Prostate Cancer: Effects on Growth in Vivo and in Vitro", *Mol. Endocrinol* (1992) 6:15–25.

(List continued on next page.)

*Primary Examiner*—Garnette D. Draper
*Assistant Examiner*—David L. Fitzgerald
*Attorney, Agent, or Firm*—Morrison & Foerster

[57] ABSTRACT

The invention is directed to recombinant DNA vectors and methods of use thereof. The vectors allow over-expression of proteins in bacterial host cells. The vectors contain a first gene encoding a ubiquitin fusion protein of interest and a second gene encoding a cytoplasmic peptidyl-prolyl cis-trans isomerase gene. Co-expression of the first and second genes allows over-expression of the protein of interest. In some cases the degree of solubility of the protein of interest is also increased.

18 Claims, 10 Drawing Sheets

OTHER PUBLICATIONS

Merz, V. W., et al., "Elevated Transforming Growth Factor–β1 and β3 mRNA Levels are Associated with ras+ myc–Induced Carcinomas in Reconstituted Mouse Prostate: Evidence for a Paracrine Role During Progression", *Mol. Endocrinol.* (1991) 5:503–513.

Okuda, S., et al., "Dietary Protein Restriction Rapidly Reduces Transforming Growth Factor β1 Expression in Experimental Glomerulonephritis", *Proc. Natl. Acad. Sci. U.S.A.* (1991) 88:9765–9769.

Yamaguchi, Y., et al., "Negative Regulation of Transforming Growth Factor–β By The Proteoglycan Decorin", *Nature* (1990) 346:281–284.

Andres, J. L., et al., "Membrane–Anchored and Soluble Forms of Betaglycan, a Polymorphic Proteoglycan That Binds Transforming Growth Factor–β", *J. Cell Biol.* (1989) 109:3137–3145.

Lin, H. Y., et al., "Expression Cloning of the TGF–β Type II Receptor, A Functional Transmembrane Serine/Threonine Kinase", *Cell* (1992) 68:775–785.

Ecker, D. J., et al., "Increasing Gene Expression in Yeast by Fusion to Ubiquitin", *J. Biol. Chem.* (1989) 264(13):7715–7719.

Standaert, R. F., et al., "Molecular Cloning and Overexpression of the Human FK506–Binding Protein FKBP", *Nature* (1990) 346:671–674.

Koltin, Y., et al., "Rapamycin Sensitivity in Saccharomyces cerevisiae Is Mediated by a Peptidyl–Prolyl cis–trans Isomerase Related to Human FK506–Binding Protein", *Mol. Cell. Biol.* (1991) 11(3):1718–1723.

Gasser, C. S., et al., "Structure and Expression of Cytosolic Cyclophilin/Peptidyl–Prolyl Cis–Trans Isomerase of Higher Plants and production of Active Tomato Cyclophilin in *Escherichia coli*", *Proc. Natl. Acad. Sci. USA* (1990) 87:9519–9523.

Holtzman, T. F., et al., "Preliminary Characterization of a Cloned Neutral Isoelectric Form of the Human Peptidyl Prolyl Isomerase Cyclophilin", *J. Biol. Chem.* (1991) 266(4):2474–2479.

Liu, J., et al., "Cloning, Expression, and Purification of Human Cyclophilin in *Escherichia coli* and Assessment of the Catalytic Role of Cysteines by Site–Directed Mutagenesis", *Proc. Natl. Acad. Sci. USA* (1990) 87:2304–2308.

Liu, J., et al., "Peptidyl–Prolyl Cis–Trans–Isomerase From *Escherichia coli*: A Periplasmic Homolog of Cyclophilin That Is Not Inhibited By Cyclosporin A", *Proc. Natl. Acad. Sci. USA* (1990) 87:4028–4032.

Allen, J. B., "Rapid Onset Synovial Inflammation and Hyperplasia Induced by Transforming Growth Factor β", *J. Exp. Med.* (1990) 171:231–247.

Armendariz–Borunda, J., et al., "Regulation of TGFβ Gene Expression in Rat Liver Intoxicated with Carbon Tetrachloride", *The FASEB Journal* (1990) 4:215–220.

Berg, D. J., "Immune Dysfunction in Mice With Plasmacytomas. I. Evidence That Transforming Growth Factor–β Contributes to the Altered Expression of Activation Receptors on Host B Lymphocytes", *J. Immunology* (1991) 146(8):2865–2872.

Bodmer, S., et al. "Immunosuppression and Transforming Growth Factor–β in Glioblastoma", *J. Immunology* (1989) 143(10):3222–3229.

Border, W. A., et al., "Transforming Growth Factor–β in Disease: The Dark Side of Tissue Repair", *J. Clin. Invest.* (1992) 90:1–7.

Broekelmann, T. J., "Transforming Growth Factor β1 is Present at Sites of Extracellular Matrix Gene Expression in Human Pulmonary Fibrosis", *Proc. Natl. Acad. Sci.* (1991) 88:6642–6646.

Castilla, A., "Transforming Growth Factors β1 and α in Chronic Liver Disease: Effects of Interferon Alfa Therapy", *New England Journal of Medicine* (1991) 324(14):933–940.

Coimbra, T., et al., "Transforming Growth Factor–β Productions in Anti–Glomerular Basement Membrane Disease in the Rabbit", *Am. J. Pathology* (1991) 138(1):223–234.

Connor, T. B., et al., "Correlation of Fibrosis and Transforming Growth Factor–β Type 2 Levels in the Eye", *J. Clin. Invest.* (1989) 83:1661–1666.

Czaja, M. J., et al., "In vitro and In Vivo Association of Transforming Growth Factor–β1 with Hepatic Fibrosis", *J. Cell Biology* (1989) 108(6) 2477–2482.

Dasch, J. R., et al., "Capture Immunoassays Specific for TGFβ1 and TGFβ2: Use in Pharmacokinetic Studies", *Annals of the new York Academy of Sciences* (1990) vol. 593, pp. 303–305.

Deguchi, Y., "Spontaneous Incrase of Transforming Growth Factor β Production by Bronchoalveolar Monomuclear Cells of Patients with Systemic Autoimmune Diseases Affected the Lung", *Annals of the Rheumatic Diseases* (1991) 51:362–365.

Fava, R., et al., "Active and Latent Forms of Transforminng Growth Factor β Activity in Synovial Effusions", *J. Exp. Med.* (1989) 169:291–296.

Glaser, B. M., et al., "Transforming Growth Factor–β2 for the Tretment of Full–Thickness Macular Holes: A Prospective Randomized Study", *Ophthalmology* (1992) 99(7)1162–173.

Khalil, N., et al., "Increased Production and Immunohistochemical Localization of Transforming Growth Factor–β in Idiopathic Pulmonary Fibrosis", *Am. J. Respir. Cell Mol. Biol.* (1991) 5:155–162.

Khalil, N., et al., "Macrophage Production of Transforming Growth Factor β and Fibroblast Collagen Synthesis in Chronic Pulmonary Inflammation", *J. Exp. Med.* (1989) 170:727–737.

Kim, S–J., et al., "Overexpression of Transforming Growth Factor–β in Transgenic Mice Carrying the Human T–Cell Lymphotropic Virus Type I tax Gene", *Mole. Cell. Biol.* (1991) 11(10):5222–5228.

Kulozik, M., et al., "Co–Localization of Transforming Growth Factor β2 with α1 (I) Procollagen mRNA in tissue Sections of Patients with Systemic Sclerosis", *J. Clin. Invest.* (1990)86:917–922.

Kunkel, T. A., "Rapid and Efficient Site–Specific Mutagenesis Without Phenotypic Selection", *Proc. Natl. Acad. Sci.* (1985) 82:488–492.

Lazdins, J. K., et al., "TGF–β: Upregulator of HIV Replication in Macrophages", *Res. Virol.* (1991) 142:239–242.

Lindholm, D., et al., "Transforming Growth Factor–β1 in the Rat Brain: Increase After Injury and Inhibition of Astrocyte Proliferation", *J. Cell Biology* (1992) 117(2):395–400.

Lotz, M., et al., "Transforming Growth Factor–β and Cellular Immune Responses in Synovial Fluids", *J. Immunology* (1990) 144(11):4189–4194.

Milani, S., et al., "Transforming Growth Factors β1 and β2 Are Differently Expressed in Fibrotic Liver Disease", *Am. J. Pathology* (1991) 139(6):1221–1229.

Ohno, I., et al., "Eosinophils in Chronically Inflamed Human Upper Airway Tissues Express Transforming Growth Factor β1 Gene (TGFβ1)", *J. Clin. Invest.* (1992)

89:1662–1668.

Peltonen, J., et al., "Evaluation of Transforming Growth Factor β and Type I Procollagen Gene Expression in fibrotic Skin Diseases by In Situ Hybridization", *J. Invest. Dermatology* (1990) 94(3):365–371.

Seed, B., et al., "Molecular Cloning of the CD2 Antigen, the T–Cell Erythrocyte Receptor, by a Rapid Immunoselection Procedure", *Proc. Natl. Acad. Sci. USA* (1987) 84:3365–3369.

Segarini, P. R., et al., "Binding of Transforming Growth Factor–β to Cell Surface Proteins Varies with Cell Type", *Molecular Endocrinology* (1989) 3(2):261–272.

Sporn, M. B., et al., "Autocrine Secretion–10 Years Later", *Annals of Internal Medicine* (1992) 117(5):408–414.

Su, H. C., et al., "A Role for Transforming Growth Factor–β1 in Regulating Natural Killer Cell and T Lymphocyte Proliferative Responses During Acute Infection With Lymphocytic Choriomeningitis Virus", *J. Immunol.* (1991) 147(8):2717–2727.

Towbin, H., et al., "Electrophoretic Transfer of Proteins from Polyacrylamide Gels to Nitrocellulose Sheets: Procedure and Some Applications", *Proc. Natl. Acad. Sci. USA* (1979) 76(9):4350–4354.

Wahl, S. M., et al., "Antagonistic and Agonistic Effects of Transforming Growth Factor–β and IL–1 in Rheumatoid Synovium", *J. Immunology* (1990) 145(8):2514–2519.

Williams, R. S., et al., "Effect of Transforming Growth Factor β on Postoperative Adhesion Formation and Intact Peritoneum", *J. Surg. Research* (1992) 52:65–70.

Wrann, M., et al., "T Cell Suppressor Factor from Human Glioblastoma Cells is a 12.5–kd Protein Closely Related to Transforming Growth Factor–β", *EMBO Journal* (1987) 6(6):1633–1636.

Tobias, J. W., et al., "Cloning and Functional Analysis of the Ubiquitin–Specific Protease Gene UBP1 of *Saccharomyces cerevisiae*" *J. Biol. Cehm.* (1991) 266(18):12021–12028.

Ito, W. et al., "Development of a Prokaryotic Expression Vector that Exploits Dicistronic Gene Organization" *Gene* (1992) 118(1):87–91.

| WCL | | EXTRACT | |
|---|---|---|---|
| 0 | 2 | S | I | kD 37-          ubi-BP3

FIG. 6

METHODS AND VECTORS FOR OVER-EXPRESSION OF UBIQUITIN FUSION PROTEINS IN HOST CELLS

CROSS-REFERENCE TO RELATED APPLICATIONS

This application is a continuation-in-part of U.S. patent application Ser. No. 08/037,597, filed Mar. 26, 1993, now abandoned.

DESCRIPTION

1. Technical Field

The present invention relates to recombinant expression systems that allow over-expression of proteins in bacterial host cells.

2. Background Art

Production of recombinant heterologous proteins in bacterial host cells is often attempted in order to produce commercially feasible amounts of protein. For industrial purposes, it is often desirable to obtain expression of heterologous proteins at levels 1–10% or more of total protein production. It is therefore essential to over-express these proteins. Unfortunately, bacterial host cells such as *E. coli* often are not ideal when used to produce such proteins. The proteins, when over-expressed, often form refractile, insoluble, "inclusion bodies" or may prove lethal to the cells. Inclusion bodies are found in the cytoplasm of the cell. Although inclusion bodies can be isolated from the cell by lysis and centrifugation, subsequent purification of the proteins involves dissolving the inclusion bodies and renaturing the proteins. Renaturation is not always effective or efficient. A variety of mechanisms have been sought to overcome these problems. However, none of the methods are universally useful.

One method of improving the soluble accumulation of foreign proteins in bacteria is to express them as fusion proteins wherein the fusion partner can be any other protein. Subsequently, the fusion partner is cleaved away from the protein of interest by enzymatic or chemical means. For instance, in the case of ubiquitin fusion proteins, the protein of interest is cleaved from ubiquitin by ubiquitin hydrolase. The cleaved ubiquitin is then purified away from the protein of interest.

The use of vectors encoding ubiquitin fusion proteins has been found to increase heterologous gene expression in yeast up to several hundred fold. Ecker et al. (1989) *J. Biol. Chem.* 264:7715–7719.

International Publication No. WO 88/02406 to Bachmair et al. describes the importance of the amino terminal amino acid residue of the protein fused carboxy terminally to ubiquitin in ubiquitin fusion proteins. All amino acid residues, with the exception of proline, allow cleavage of ubiquitin from the fusion protein. Specific cleavage is important because it produces a defined amino terminus for the protein of interest. Varshavsky et al. (1991) *J. Biol. Chem.*, 266:12021–12028 have described ubiquitin hydrolases from yeast capable of performing this function. International Publication No. WO 89/12678 to Liu et al. describes a purification scheme for a different ubiquitin hydrolase.

Peptidyl-prolyl cis-trans isomerases (PPIs), catalyze rotation of the peptide bond on the amino side of proline residues and facilitates in vivo protein folding. One family of PPIs is termed "cyclophilins". Cyclophilins bind to the immunosuppressive agent cyclosporin A with high affinity. Another PPI is FKBP which binds to the immunosuppressive agent FK506. Standaert et al. (1990) *Nature*, 346:671–674. Yet another PPI is the yeast RBPI which binds to both rapamycin and FK506. Koltin et al. (1991) *Mol. Cell. Biol.*, 11:1718–1723.

Cyclophilin-encoding genes are expressed in a variety of organisms including humans, rats, hamsters, yeast, *Neurospora crassa, Drosophila melanogaster* and tomatoes. Protein coded by tomato cyclophilin genes expressed in *E. coli* was found mainly in inclusion bodies, but some activity was detected in the soluble fraction. Gasser et al. (1990) *Proc. Natl. Acad. Sci. USA*, 87:9519–9523. Cloning and expression of a human cyclophilin in *E. coli* has also been reported. Holtzman et al. (1991) *J. Biol. Chem.*, 266:2474–2479. Expression of a cloned human cyclophilin in *E. coli* has been shown to result in 40% of the cyclophilin in the soluble fraction. Liu et al. (1990) *Proc. Natl. Acad. Sci. USA*, 87:2304–2308.

An *E. coli* PPI, termed "rotamase", has been found to be located in the periplasmic space where it is thought to function in refolding of secreted proteins. Liu and Walsh (1990) *Proc. Natl. Acad. Sci. USA*, 87:4028–4032. Liu and Walsh cloned and over-expressed *E. coli* PPI; they found that it was homologous to human cyclophilin but not sensitive to cyclosporin A. Moreover, this *E. coli* gene encodes a signal peptide, indicating that the protein is secreted.

SUMMARY OF THE INVENTION

The invention is directed to recombinant DNA vectors and methods of use thereof. The vectors allow over-expression of proteins in bacterial host cells. The vectors contain a first gene encoding a protein of interest optionally fused to ubiquitin and a second gene encoding a cytoplasmic peptidyl-prolyl cis-trans isomerase. Co-expression of the first and second genes allows over-expression of the protein of interest. In all cases tested, the degree of solubility of the protein is also increased.

BRIEF DESCRIPTION OF THE DRAWINGS

FIG. 1 is described in Example 1.

FIG. 2 is described in Example 1.

FIG. 3 is discussed in Example 2.

FIGS. 4–9 show Coomassie-stained gels of Whole Cell Extracts (WCL) before (0) or after (2) induction with IPTG, as well as extracts from the induced cells, which include a soluble fraction (S) and an insoluble fraction (I). The center M panels where included have molecular weight markers. FIG. 4 shows results obtained with plasmids 16926 (left panels) and 16927 (right panels) which demonstrate the solubility of ubiquitin-IGF-I fusion protein from 30° C. cultures.

FIG. 5 shows results obtained with plasmid 12880 which demonstrate the solubility of met-IGFBP-3 fusion protein from 30° C. cultures.

FIG. 6 shows results obtained with plasmid 12875 which demonstrate the superior solubility of the ubiquitin-IG- FBP-3 fusion protein from 30° C. cultures.

FIG. 7 shows the results obtained with plasmid 16921, which demonstrates the high solubility of a fusion of ubiquitin with the soluble extracellular domain of the Type II TGF-β receptor from 30° C. cultures.

FIG. 8 shows the results obtained with plasmid 16918 which demonstrates the relatively low solubility of met-TGF-β2 fusion protein from 37° cultures.

FIG. 9 shows results obtained with plasmid 16920 which demonstrates that the ubiquitin-TGF-β2 fusion is more soluble, especially with the cyclophilin gene.

DETAILED DESCRIPTION OF THE INVENTION

Figure 1:
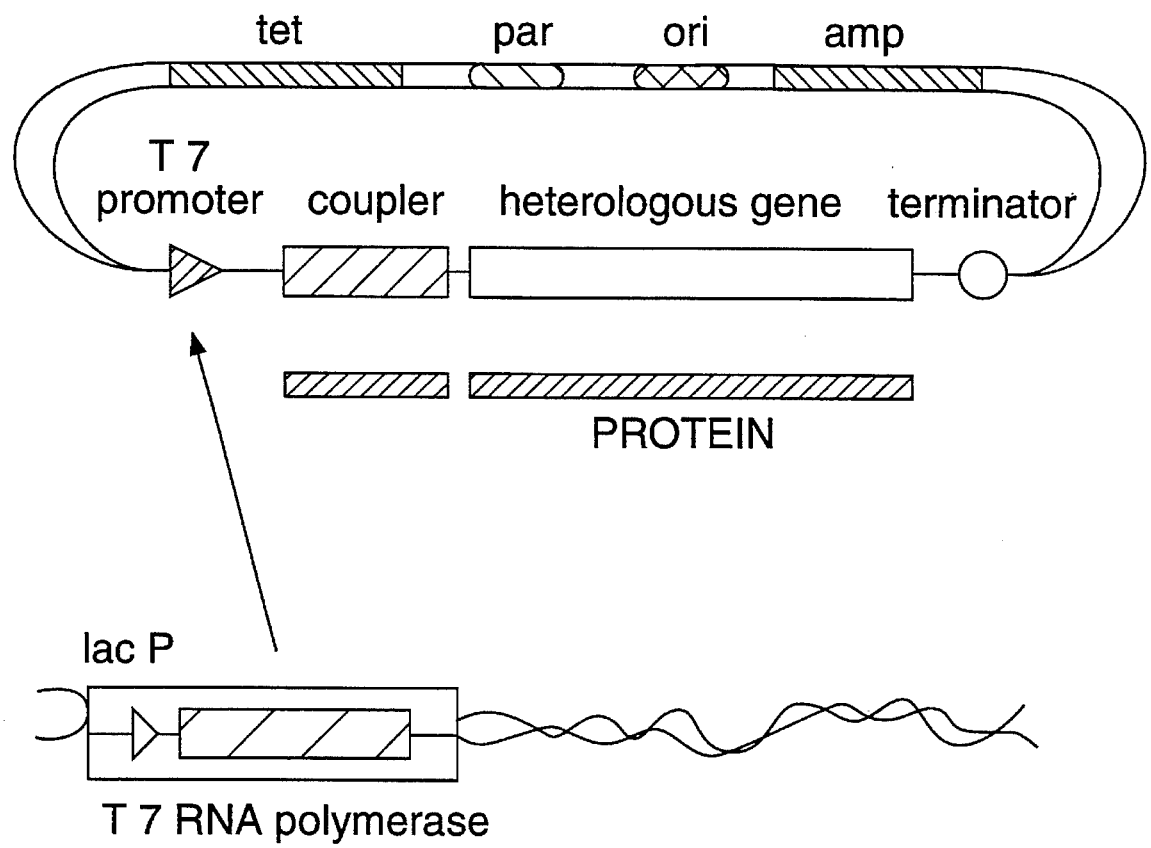
FIG. 1 is a line diagram depicting a plasmid vector used for heterologous gene expression in *E. coli* W3110DE3.

It has now been found that genes which could not previously be over-expressed and accumulated in soluble form within bacterial host cells can now be so expressed when coded for by vectors such as those described herein.

The invention includes recombinant DNA vectors containing a first gene encoding the protein of interest optionally fused to ubiquitin and a second gene encoding a cytoplasmic peptidyl-prolyl cis-trans isomerase (PPI). Concomitant expression of the first and second genes allows over-expression of the protein of interest. The DNA vectors are substantially pure polynucleotides.

An "isolated" or "substantially pure" polynucleotide is a polynucleotide, e.g., an RNA, DNA, or a mixed polymer, which is substantially separated from other polynucleotide sequences which naturally accompany a native sequence. The term embraces a polynucleotide sequence which has been removed from its naturally occurring environment, and includes recombinant or cloned DNA isolates and chemically synthesized analogues or analogues biologically synthesized by heterologous systems.

A polynucleotide is said to "encode" a polypeptide if, in its native state or when manipulated by methods known in the art, the polynucleotide can be transcribed and/or translated to produce the polypeptide of a fragment thereof. The anti-sense strand of such a polynucleotide is also said to encode the polypeptide.

Polynucleotide sequences are operably linked when they are placed into a functional relationship with another polynucleotide sequence. For instance, a promoter is operably linked to a coding sequence if the promoter affects transcription or expression of the coding sequence. Generally, operably linked means that the linked sequences are contiguous and, where necessary to join two protein coding regions, both contiguous and in reading frame. However, it is well known that certain genetic elements, such as enhancers, may be operably linked even at a distance, i.e., even if not contiguous.

The term "recombinant" polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Large amounts of the polynucleotides may be produced by replication in a suitable host cell. Natural or synthetic DNA fragments coding for proteins or fragments thereof will be incorporated into recombinant polynucleotide constructs, typically DNA constructs, capable of introduction into and replication in a prokaryotic or eukaryotic cell. Usually the construct will be suitable for replication in a unicellular host, such as yeast or bacteria; but the construct may also be intended for introduction to, with or without an integration within, the genome of eukaryotic cells.

The polynucleotides may also be produced by chemical synthesis, including, but not limited to, the phosphoramidite method described by Beaucage and Carruthers (1981) *Tet. Lett.*, 22:1859–1862 and the triester method according to Matteucci et al. (1981) *J. Am. Chem. Soc.*, 103:3185. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

DNA constructs prepared for introduction into a host will typically comprise a replication system recognized by the host, including the intended DNA fragment encoding the desired polypeptide, and will preferably also include transcription and translational initiation regulatory sequences operably linked to the polypeptide encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

The appropriate promoter and other necessary vector sequences are selected so as to be functional in the host. Examples of workable combinations of cell lines and expression vectors include but are not limited to those described in *Molecular Cloning: A Laboratory Manual*, 2nd ed., Vol. 1–3, ed. Sambrook, et al., Cold Spring Harbor Laboratory Press (1989) or *Current Protocols in Molecular Biology*, ed. F. Ausubel et al., Greene Publishing and Wiley-Interscience: New York (1987 and periodic updates); and Metzger et al. (1988), *Nature*, 334:31–36. Many useful vectors for expression in bacteria, yeast, mammalian, insect, plant or other cells are known in the art and may be obtained from vendors including but not limited to Stratagene, New England Biolabs, Promega Biotech, and others. In addition, the construct may be joined to an amplifiable gene (e.g., DHFR) so that multiple copies of the gene may be obtained. For appropriate enhancer and other expression control sequences see also *Enhancers and Eukaryotic Gene Expression*, Cold Spring Harbor Press, N.Y. (1983). While such expression vectors may replicate autonomously, they may less preferably replicate by being inserted into the genome of the host cell, by methods known in the art.

Expression and cloning vectors will likely contain a selectable marker, a gene encoding a protein necessary for the survival or growth of a host cell transformed with the vector, although such a marker gene may be carried on another polynucleotide sequence co-introduced into the host cell. Only those host cells expressing the marker gene will survive and/or grow under selective conditions. Typical selection genes include but are not limited to those encoding proteins that (a) confer resistance to antibiotics or other toxic substances, e.g. ampicillin, tetracycline, etc.; (b) complement auxotrophic deficiencies; or (c) supply critical nutrients not available from complex media. The choice of the proper selectable marker will depend on the host cell, and appropriate markers for different hosts are known in the art.

The vectors containing the polynucleotides of interest can be introduced into the host cell by any method known in the art. These methods vary depending upon the type of cellular host, including but not limited to transfection employing calcium chloride, rubidium chloride, calcium phosphate, DEAE-dextran, other substances, and infection by viruses.

Large quantities of the polynucleotides and polypeptides of the present invention may be prepared by expressing the polynucleotides of the present invention in vectors or other expression vehicles in compatible host cells. The most commonly used prokaryotic hosts are strains of *Escherichia coli*, although other prokaryotes, such as *Bacillus subtilis* may also be used.

The genes encoding the protein of interest are preferably chimeric, that is, they encode a fusion protein. Preferably the chimeric genes encode a fusion protein containing ubiquitin and the protein of interest. More preferably, the chimeric gene encodes a ubiquitin-TGF-β fusion protein, a ubiquitin-IGF fusion protein, a ubiquitin-IGFBP-3 fusion protein, or a ubiquitin-sβ-RII fusion protein (i.e., a fusion with the soluble extracellular domain of the Type II TGF-β receptor protein). The ubiquitin chimeric genes are operably linked so that ubiquitin is the amino-terminal portion of the protein and so that cleavage of ubiquitin yields the protein of interest.

Examples of other PPIs include but are not limited to cyclophilins, FKP, RBPI and rotamase. PPIs can be obtained from a variety of sources, including but not limited to humans, rats, hamsters, yeast, *Neurospora crassa*, *Drosophila melanogaster* and tomatoes. Preferably, the PPI is rotamase obtained from *E. coli*.

The invention also includes methods for over-expression of the protein of interest in a bacterial host. The methods include expressing the gene encoding the protein of interest in the host cell and concomitantly expressing a gene encoding a cytoplasmic PPI in the host cell. It is preferred that the PPI remain in the cytoplasm once it is expressed. This can be accomplished by expressing a PPI normally found in the cytoplasm or by removing or disabling the signal peptide of a secreted form of PPI. The cells can then be treated to recover the protein of interest and the protein can be subject to further purification techniques.

Preferably the host cells are a strain of *E. coli*, more preferably they are *E. coli* W3110DE3. The genes encoding the proteins of interest are preferably chimeric. Preferably the chimeric genes encode fusion proteins containing ubiquitin and the protein of interest. More preferably, the chimeric gene encodes a ubiquitin-TGF-β fusion protein, a ubiquitin-IGF fusion protein, a ubiquitin-IGFBP-3 fusion protein or a ubiquitin-sβ-RII protein. Preferably, the PPI is *E. coli* rotamase lacking a signal peptide.

The recombinant nucleic acid sequences used to produce fusion polypeptides and PPI of the present invention may be derived from natural or synthetic sequences. The nucleotide sequences and amino acid sequences and/or fragments thereof may be obtained from GENBANK and/or the Swiss Protein Database, with the database accession numbers as follows:

| Gene | GENBANK | Swiss-Prot |
|---|---|---|
| IGF | HUMIGFI | |
| | SYNHUMGFIS | |
| ubiquitin | YSCUBI1G | UBIQ_YEAST |
| | YSCUBI2G | |
| | YSCUBI3G | |
| | YSCUBI4G | |
| ubiquitin hydrolase | YSCUBP1 | |
| TGF-β | HUMTGFB2A | TGF2_HUMAN |
| sβ-RII | HUMTGFBIIR | |
| IGFBP-3 | HUMGFIBPA | IBP3_HUMAN |

Codon-optimized genes may be employed.

The invention further includes a method of producing a soluble, or more soluble, protein in a bacterial host. The methods include expressing the gene encoding the protein of interest in the host cell and concomitantly expressing a gene encoding peptidyl-prolyl cis-trans isomerase in the host cell. The cells can then be treated to remove the protein of interest and the protein can be subject to further purification techniques. In the case of ubiquitin fusion proteins, the proteins are purified by conventional purification methods, the ubiquitin is then cleaved from the protein of interest and the two resulting molecules are separated from each other by further purification.

The following examples are meant to illustrate but not limit the invention. Unless otherwise mentioned, the DNA cloning and expression methods are essentially as described in Sambrook et al. (1989).

EXAMPLE 1

Vectors Encoding Ubiquitin Fusion Proteins

The expression vectors used in this work were similar to pJU1003, described by Squires et al. (1988) *J. Biol. Chem.*, 263:16297–16302, except that genes inserted downstream of the translational coupler and initiation codon coded for mature human IGF-1 (70 aa), IGFBP-3 (264 aa), TGF-β2 (112 aa) or the soluble extracellular domain of the Type II TGF-β receptor (136 aa).

These plasmids also differ from pJU1003 in that (a) they do not contain the synthetic 16 base pair (bp) adaptor sequence at the 5' end of the tet gene in pJU1003 and (b) they contain a DNA insertion at the unique PvuII site in the pBR322-derived backbone: a 385 bp fragment carrying the par locus of pSC101. Meacock and Cohen (1980) *Cell*, 20:529–542.

Each gene is prepared for expression in two separate configurations: (1) with a methionine initiation codon attached to the coding sequence or (2) with the 76 codons of yeast ubiquitin inserted in-frame upstream of the gene sequence (FIG. 1).

Figure 2:
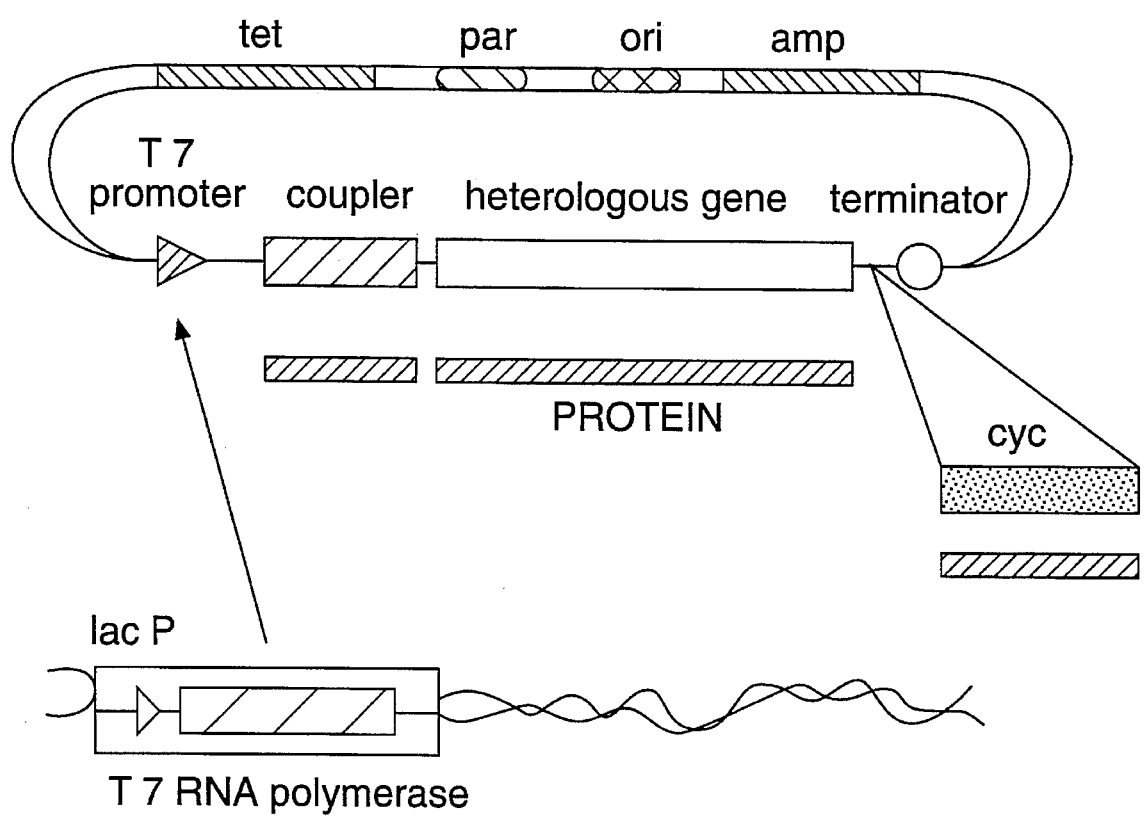
FIG. 2 is a line diagram depicting a vector used for heterologous gene expression in *E. coli* W3110DE3.

Optionally, each gene configuration is further modified by placing the coding sequence for *E. coli* periplasmic rotamase minus its signal sequence downstream such that the rotamase gene is expressed as an independent polypeptide but under the control of the same promoter. The signal peptide of the rotamase gene has been deleted as described by Liu and Walsh (1990) *Proc. Natl. Acad. Sci. USA*, 87:4028–4032 and replaced with an initiator methionine codon (FIG. 2).

Thus, each gene is expressed in four possible configurations. In addition, vectors 12886 and 12887 in which the gene is deleted and replaced with a linker (5' . . . GGATCCCGTGGAGGATTAAACCATGGATGCAT- AAGCTTCGAATTCTGCCAGGCATG-
CAAGCTCAGATCC . . . 3' (SEQ ID NO:1)) are used as
controls. The plasmid designations are shown in Table 1:

TABLE 1

| CONFIGU-RATION | GENE | | | | |
|---|---|---|---|---|---|
| | None | IGF-1 | IGFBP3 | TGFβ2 | TGFR |
| Gene alone | 12886 | 13049 | 12833 | 16918 | 16919 |
| Gene + rotamase | 12887 | n.d. | 12880 | 16923 | 16924 |
| Ubi-gene | n.d. | 16926 | 12873 | 16916 | 16917 |
| Ubi-gene + rotamase | n.d. | 16927 | 12875 | 16920 | 16921 |

In brief, sequences for yeast ubiquitin and rotamase were obtained using PCR-mediated amplification from the appropriate genomic DNAs. cDNA clones for IGFBP-3 were isolated as described by Spratt et al. (1990) *Growth Factors* 3:63–72 and further modified by substituting the amino-terminal one third of the gene with a synthetic DNA sequence encoding the same amino acids as the natural gene but using codons optimized for expression in *E. coli*. The IGF-1 sequence was constructed de novo from synthetic DNA and also used codons optimized for *E. coli*. The TGF-β2 sequence was obtained by PCR-mediated modification of a cDNA clone obtained from Dr. Michael Sporn, NIH. The sβ-RII sequence was similarly derived from pH2-3FF, a cDNA clone from Dr. Herb Lin, MIT. All PCR-derived DNAs were sequenced prior to use.

*E. coli* K-12 strain W3110 was obtained from B. Bachmann, ECGSC, Yale University. It was lysogenized with the DE3 defective phage as described by Studier and Moffat (1986) *J. Mol. Biol.*, 189:113–130. W3110DE3 was one such lysogen. It was used as the host strain for all experiments described.

Each plasmid was introduced into W3110DE3 by calcium-mediated transformation and selection for ampicillin resistance.

EXAMPLE 2

Effect of Rotamase Co-Expression on Growth Rate of Strains Expressing Ubiquitin Fusion Proteins Each bacterial strain containing one of the above plasmids was inoculated into 5 ml Luria Broth containing tetracycline (15 µg/ml) and grown to saturation overnight with aeration at 37° C. 2 ml of this fresh culture was diluted into 100 ml of LB with tetracycline and an additional 0.2% glucose, and aerated for several hours and the optical density of the culture was followed at 600 nm through the logarithmic growth phase. Mean generation times were calculated from semilogarithmic plots of cell density during this phase of growth only. The values obtained for 17 strains are shown in FIG. 3.

Figure 3:
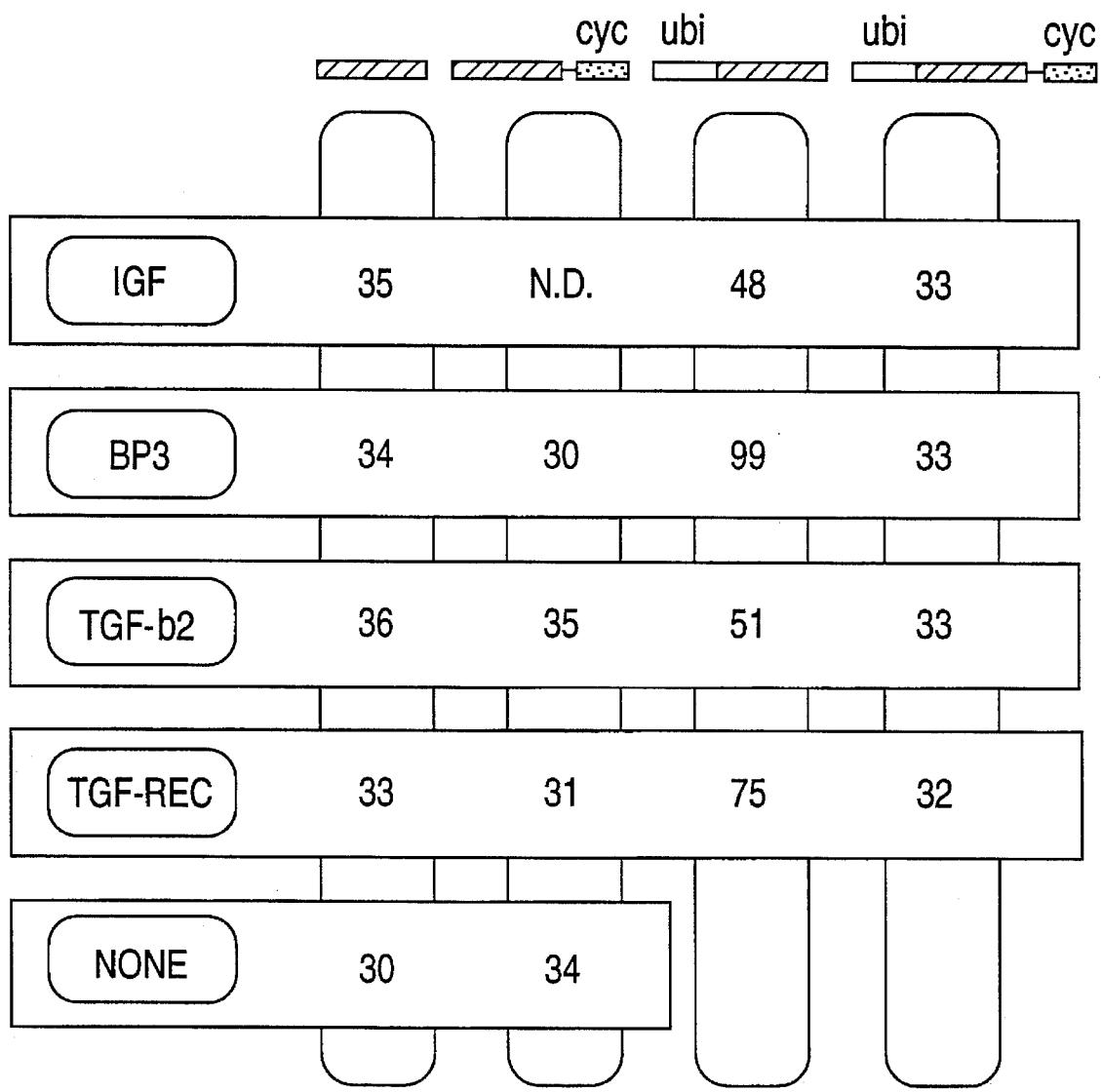
FIG. 3 summarizes the mean generation times for *E. coli* W3110DE3 carrying the various recombinant DNA constructs as indicated.

As seen in FIG. 3, in each case (all four genes), ubiquitin fusion constructs markedly increased the generation time of the host strain which was overcome by the inclusion of the rotamase gene in the same operon, downstream of the gene of interest.

EXAMPLE 3

Fusion Protein Solubility

The cells were grown as described in Example 2 except that some cells were grown at 30° C. and followed through early logarithmic growth until the optical density at 600 nm reached 0.4. At this point, a 1 ml aliquot was removed and these cells were harvested by centrifugation (0 time point). Isopropyl-thiogalacto-pyranoside (IPTG) was added to a final concentration of 0.4 mM to initiate expression of the recombinant genes and incubation of the culture was continued for two hours. A second aliquot of cells was removed at a 2 hr time point. The remainder of the culture was harvested by centrifugation, resuspended in 50 mM Tris-Cl, pH 8.0, 2 mM EDTA (disruption buffer) and cells were disrupted by sonication using a Branson sonifier (2×30 sec bursts). Optionally, lysis was enhanced by adding 0.2 mg/ml chicken lysozyme to the disruption buffer. The soluble fraction (supernatant) was obtained after centrifugation in a Beckman TJ-6 centrifuge at 3000 rpm for 15 min at 4° C. The pellet was further resuspended in an equal volume of disruption buffer for analysis.

Whole cell extracts were prepared for electrophoresis in 12 or 18% polyacrylamide gels by resuspending whole cells in sample buffer and boiling for 5 min. Soluble and insoluble fraction samples were prepared by adding 1/10th volume 10× sample buffer and incubating at 65° C. for 15 min (1% SDS, 10% glycerol, and 0.1% bromphenol blue). The gels were run according to the method described by Laemmli (1970) *Nature*, 227:680–685.

The results showed that, in all cases, ubiquitin fusion enhances accumulation of the desired protein in the soluble fraction, particularly when the cells are grown at 30° C. In each case, the identity of the major induced protein was confirmed by Western Blotting (data not shown).

Figure 4:
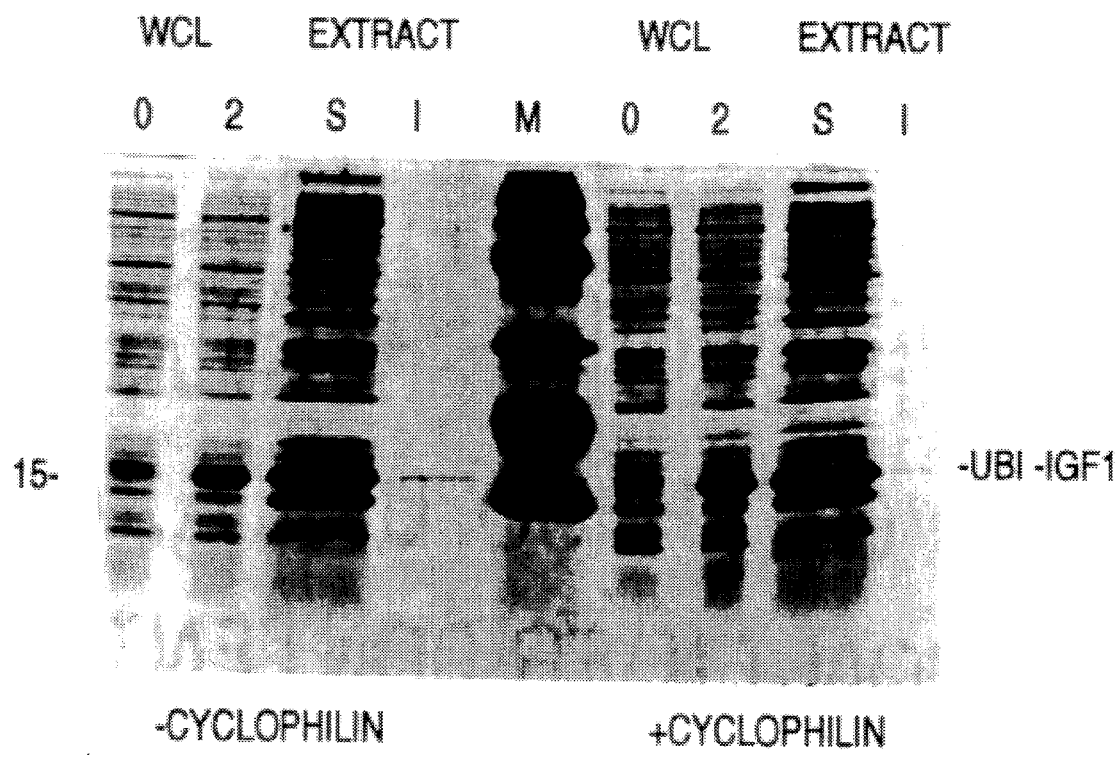

FIG. 4 shows that the ubiquitin-IGF fusions expressed by the vectors 16926 and 16927 are extremely soluble (at least 90% of the major protein product of 15 kD observed after induction is in the soluble fraction). The solubility was further increased when the ubiquitin fusion was co-expressed with rotamase. When met-IGF (without ubiquitin) was expressed in a similar system, no IGF could be seen in the soluble fraction (data not shown).

Figure 5:
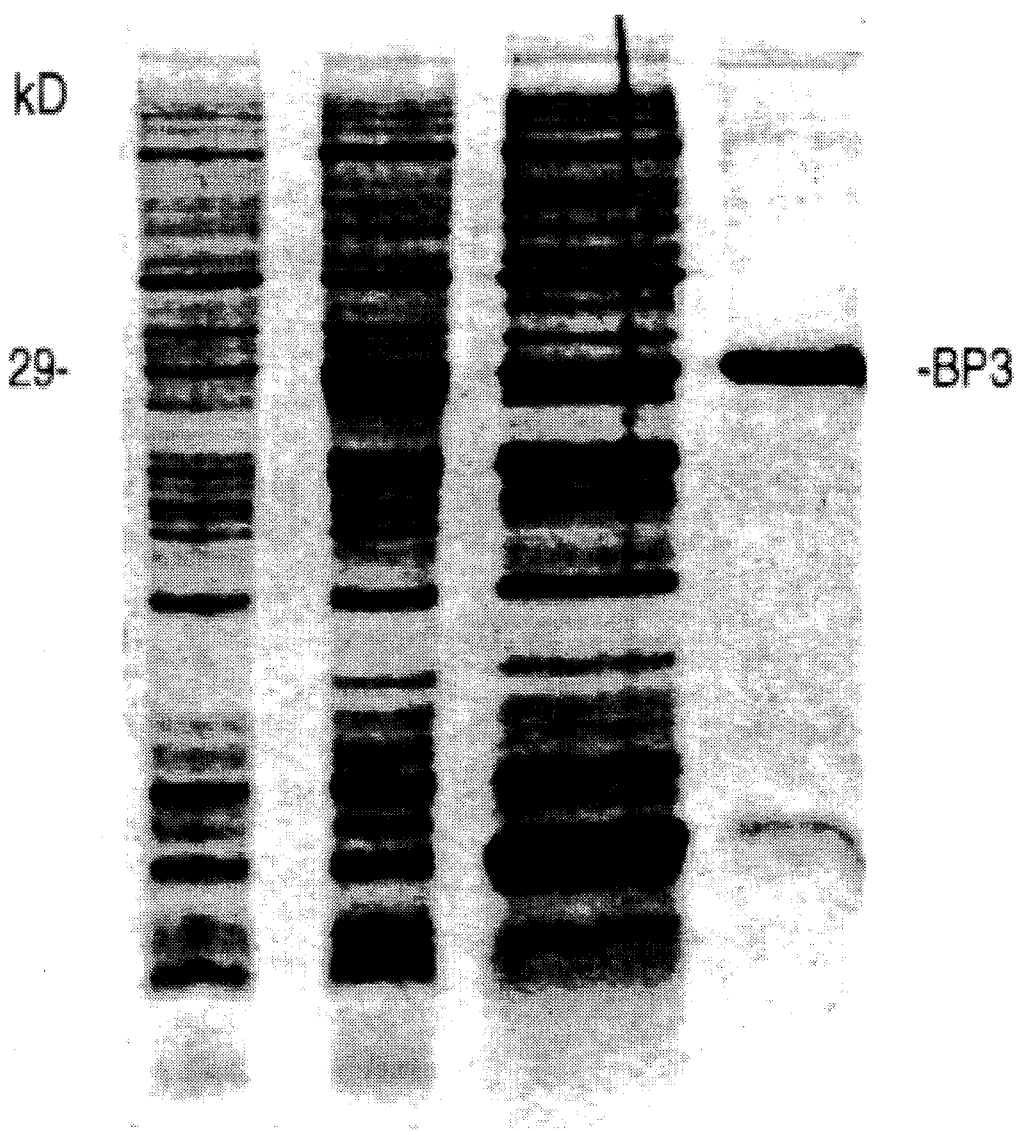
Figure 6:
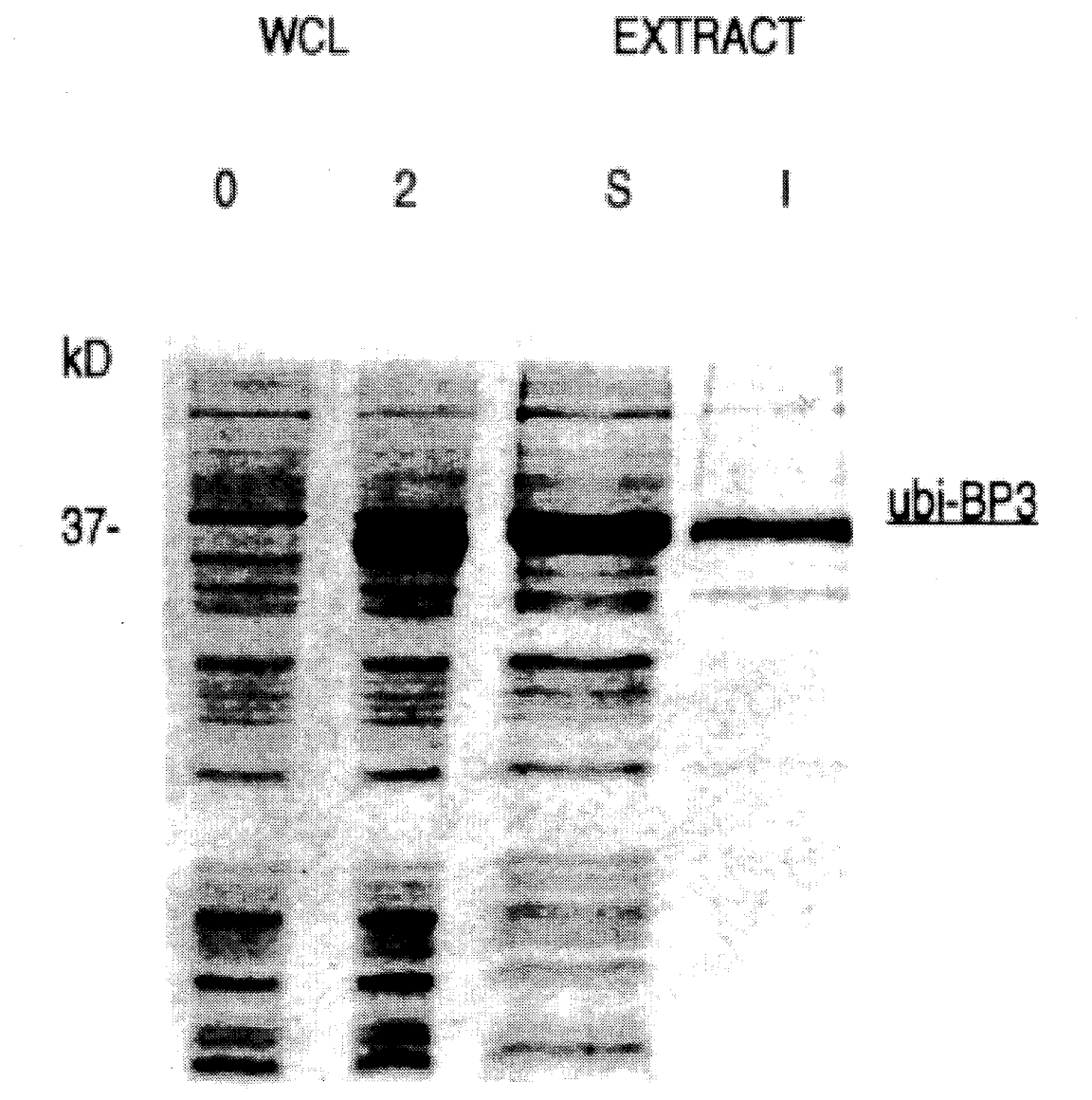

FIGS. 5 and 6 show the dramatic improvement in the solubility of IGFBP-3 conferred by the ubiquitin fusion partner. In FIG. 5, the met-IGFBP-3 product (29 kD) can be seen primarily in the insoluble fraction. In FIG. 6, the ubiquitin-IGFBP-3 fusion (37 kD) is primarily in the soluble fraction.

Figure 7:
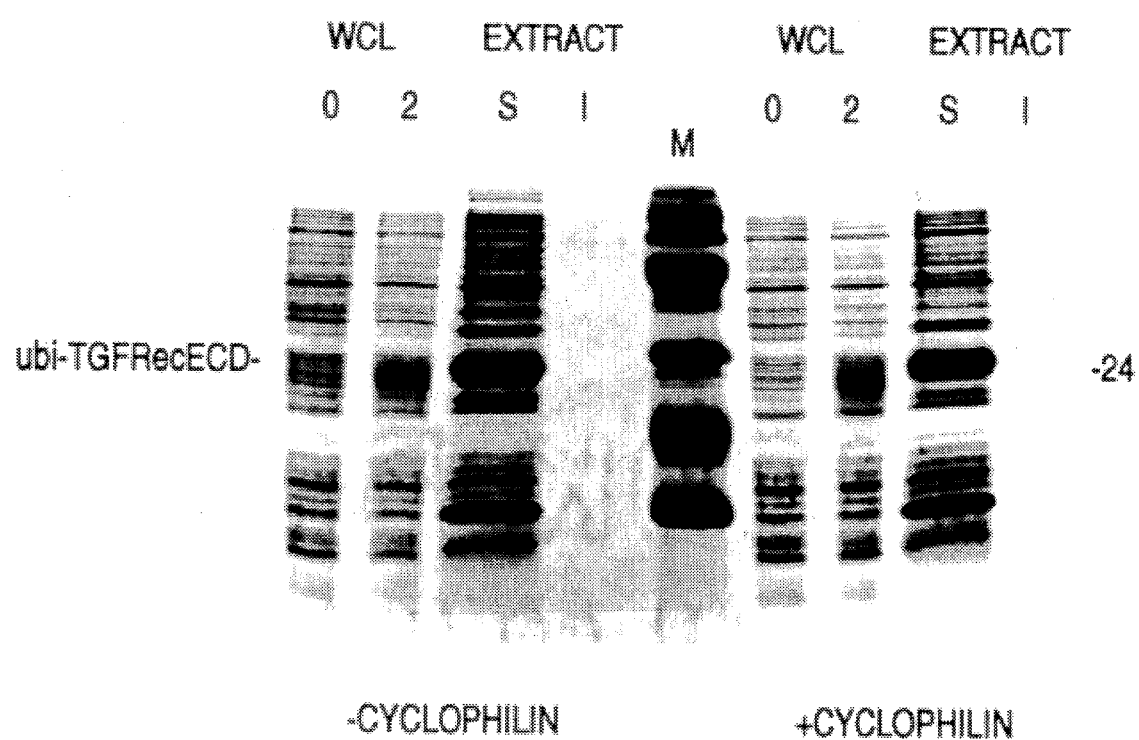

Yet another example of the dramatic effects of ubiquitin fusion on protein solubility is shown in FIG. 7. The ubiquitin-sβ-RII fusion protein (24 kD) accumulates primarily in the soluble fraction. In this case, the ubiquitin fusion is so soluble, that no effect can be discerned for rotamase.

Figure 8:
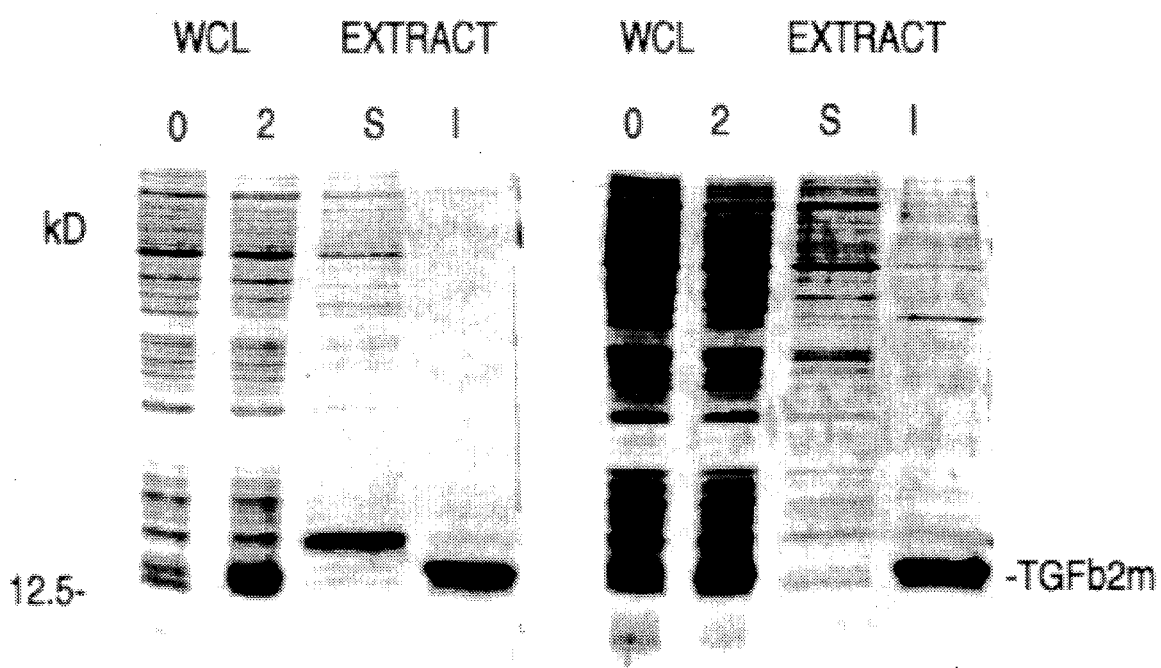
Figure 9:
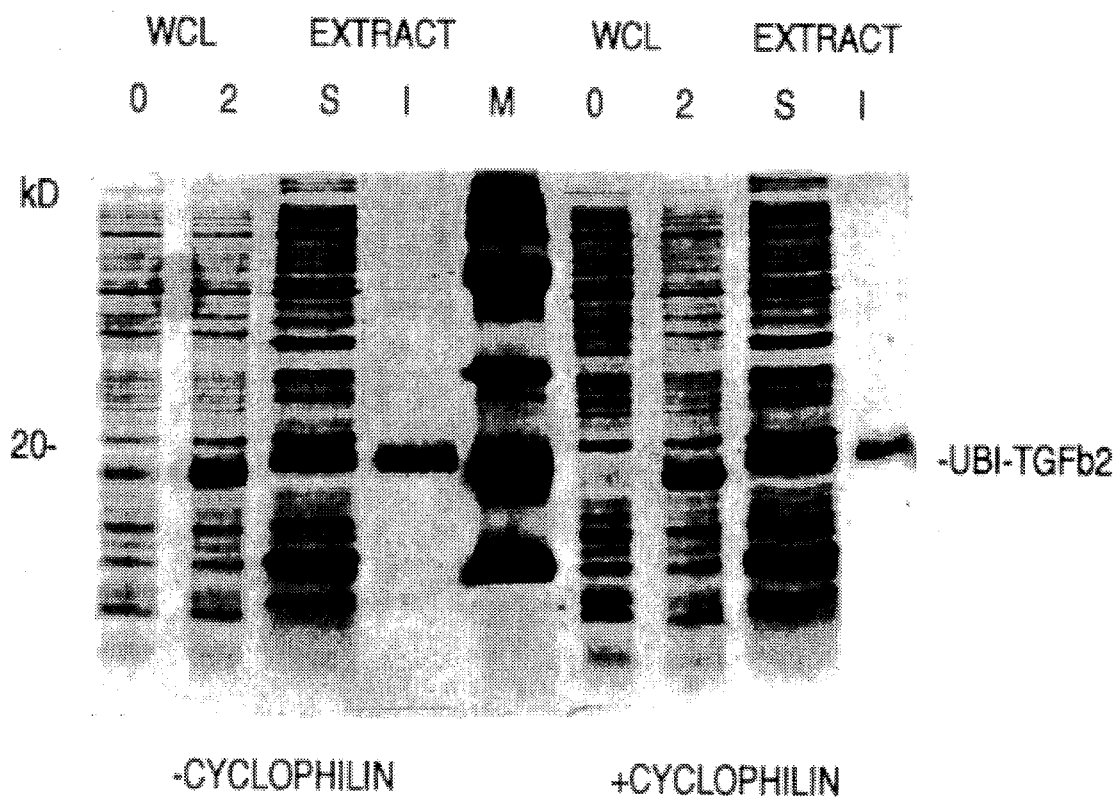

Mature TGF-β2 is well known in the art as a notoriously insoluble protein in aqueous environments, even when correctly folded. For example, when expressed as a met-TGF-β2 protein at 37° C., the protein is entirely insoluble (FIG. 8). The left panels of FIG. 8 show results obtained when lysozyme is used to lyse cells; the right panels show the identical experiment without lysozyme. In contrast, when TGF-β2 is fused to ubiquitin (the 20 kD band in FIG. 9), TGF-β2 largely accumulates in the soluble fraction, particularly when co-expressed with rotamase (right panels).

Figure 10:
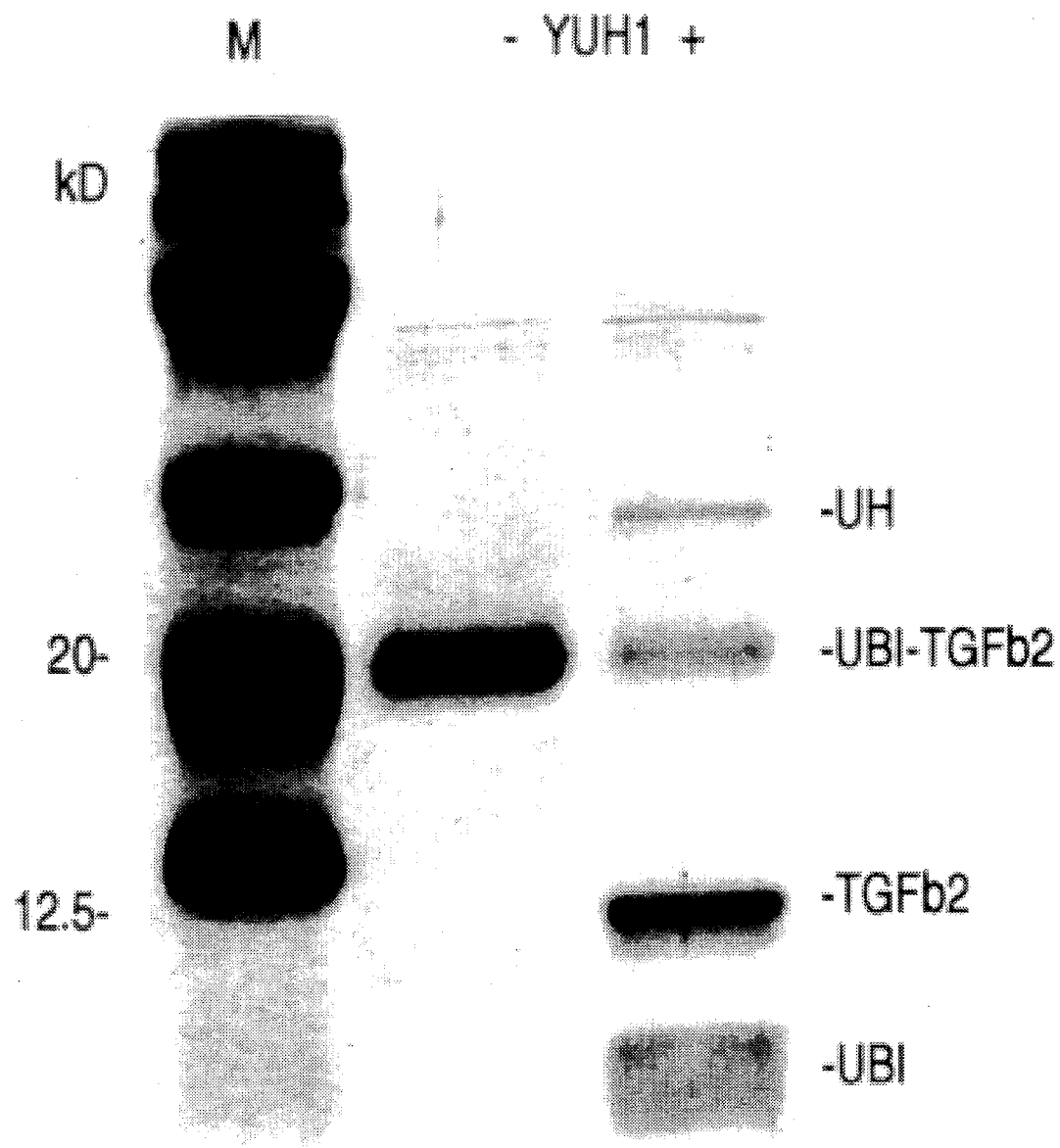
FIG. 10 shows a Coomassie-stained gel with ubiquitin-TGF-β2 before and after cleavage with ubiquitin hydrolase YUH-1 and demonstrates that the ubiquitin-TGF-β 2 fusion protein is cleaved with ubiquitin hydrolase YUH-1.

Ubiquitin fusions were also cleaved enzymatically to release the desired molecule according to the methods described by Tobias and Varshafsky (1991) *J. Biol. Chem.* 266:12021–12028; and Miller et al. (1989) *Biotechnology* 7:698–704. One example is shown in FIG. 10 which shows that the cleavage of ubiquitin-TGF-β2 fusion protein of FIG. 9 produce the desired two fragments, TGF-β2 (12.5 kD) and ubiquitin (8 kD). FIG. 10 shows a Coomassie-stained gel with ubiquitin-TGF-β2 fusion before and after cleavage with ubiquitin hydrolase YUH-1. The left panel shows molecular weight markers. The middle and right panels show results without and with YUH-1 cleavage, respectively. The protein bands are approximately the expected sizes: ubiquitin hydrolase (about 30 kD), fusion protein (about 20 kD), TGF-β2 (about 12.5 kD) and ubiquitin (about 8 kD). This result demonstrates that cleavage is accurate and yields the protein of interest.

All publications and patent applications mentioned in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

decreased relative to that of an otherwise identical host cell expressing said first gene but not said second gene.

8. The method according to claim 7, wherein the peptidyl-prolyl cis-trans isomerase gene encodes *E. coli* rotamase lacking a functional signal peptide.

9. The method according to claim 7, wherein the first gene consists of DNA encoding ubiquitin and DNA encoding a TGF-β, wherein expression of the gene results in production of a ubiquitin-TGF-β fusion protein.

10. The method according to claim 7, wherein the first gene consists of DNA encoding ubiquitin and DNA encoding an IGF, wherein expression of the gene results in production of a ubiquitin-IGF fusion protein.

11. The method according to claim 7, wherein the first gene consists of DNA encoding ubiquitin and DNA encoding IGFBP-3, wherein expression of the gene results in production of a ubiquitin-IGFBP-3 fusion protein.

12. The method according to claim 7, wherein the first

I claim:

1. A recombinant DNA vector comprising a first gene encoding a fusion protein between ubiquitin and a protein of interest and a second gene encoding a cytoplaemic peptidyl-prolyl cis-trans isomerase such that the vector is capable of directing the co-expression of the first and second genes.

2. The vector according to claim 1, wherein the peptidyl-prolyl cis-trans isomerase gene encodes *E. coli* rotamase lacking a functional signal peptide.

3. The vector according to claim 1, wherein the the protein of interest is a transforming growth factor-beta (TGF-β).

4. The vector according to claim 1, wherein the protein of interest is an insulin-like growth factor (IGF).

5. The vector according to claim 1, wherein the protein of interest is insulin-like growth factor binding protein-3 (IGFBP-3).

6. The vector according to claim 1, wherein the protein of interest is the soluble extracellular domain of the Type II TGF-β receptor (sβ-RII).

7. A method of expressing a ubiquitin fusion protein in an *E. coli* host cell comprising the steps of:
    a. expressing a first cloned gene encoding the ubiquitin fusion protein in the host; and
    b. concomitantly expressing a second cloned gene encoding a cytoplasmic peptidyl-prolyl cis-trans isomerase; whereby the mean generation time of said host cell is gene consists of DNA encoding the soluble extracellular domain of the Type II TGF-β receptor (sβ-RII), wherein expression of the gene results in production of a ubiquitin-sβ-RII fusion protein.

13. A method of producing a soluble protein comprising the steps of:
    a. expressing a first cloned gene encoding the ubiquitin fusion protein in an *E. coli* host cell; and
    b. concomitantly expressing a second cloned gene encoding a cytoplasmic peptidyl-prolyl cis-trans isomerase, whereby the mean generation time of said host cell is decreased relative to that of an otherwise identical host cell expressing said first gene but not said second gene; and
    c. cleaving the ubiquitin moiety from the fusion protein to yield the soluble protein.

14. The method according to claim 13, wherein the peptidyl-prolyl cis-trans isomerase gene encodes *E. coli* rotamase lacking a functional signal peptide.

15. The method according to claim 13, wherein the first gene consists of DNA encoding ubiquitin and DNA encoding a TGF-β, wherein expression of the gene results in production of a ubiquitin-TGF-β fusion protein.

16. The method according to claim 13, wherein the first gene consists of DNA encoding ubiquitin and DNA encoding an IGF, wherein expression of the gene results in production of a ubiquitin-IGF fusion protein.

17. The method according to claim 13, wherein the first gene consists of DNA encoding ubiquitin and DNA encoding IGFBP-3, wherein expression of the gene results in production of a ubiquitin-IGFBP-3 fusion protein.

18. The method according to claim 13, wherein the first gene consists of DNA encoding ubiquitin and DNA encoding the soluble extracellular domain of the Type II TGF-β receptor (sβ-RII), wherein expression of the gene results in production of a ubiquitin-sβ-RII fusion protein.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGATCCCGTG  GAGGATTAAA  CCATGGATGC  ATAAGCTTCG  AATTCTGCCA  GGCATGCAAG        60

CTCAGATCC                                                                    69
```